US006403634B1

(12) United States Patent
Bissery

(10) Patent No.: US 6,403,634 B1
(45) Date of Patent: *Jun. 11, 2002

(54) USE OF TAXOID DERIVATIVES

(75) Inventor: Marie-Christine Bissery, Vitry Sur Seine (FR)

(73) Assignee: Aventis Pharma S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,015

(22) Filed: Jan. 13, 2000

Related U.S. Application Data

(60) Provisional application No. 60/121,333, filed on Feb. 23, 1999.

(30) Foreign Application Priority Data

Jan. 13, 1999 (EP) ............................................. 99400072

(51) Int. Cl.⁷ ............................................ A61K 31/335
(52) U.S. Cl. ...................................................... 514/449
(58) Field of Search ......................................... 514/449

(56) References Cited

U.S. PATENT DOCUMENTS

| 5,637,723 A | 6/1997 | Commercon et al. |
| 5,847,170 A | * 12/1998 | Bouchard et al. ........... 549/510 |
| 5,962,705 A | 10/1999 | Didier et al. |

FOREIGN PATENT DOCUMENTS

EP 0 617 018 A1 9/1994

OTHER PUBLICATIONS

Paul Caubère, "Unimetal Super Bases," *Chemical Reviews*, vol. 93, No. 6, pp. 2317–2334 (1993).
T. H. Corbett; D.P. Griswold, Jr.; B.J. Roberts; J.C. Peckham; and F. M. Schabel, Jr., "Evaluation of Single Agents and Combinations of Chemotherapeutic Agents in Mouse Colon Carcinomas," *Cancer*, vol. 40, No. 5, pp. 2660–2680 (Nov. 1977).
Manfred Schlosser, "Superbases as Powerful Tools in Organic Syntheses," *Mod. Synth. Methods*, vol. 6, pp. 227–271 (1992).
Frank M. Schabel, Jr.,; Daniel P. Griswold, Jr.; Thomas H. Corbett; W. Russell Laster, Jr.; Joseph G. Mayo; and Harris H. Lloyd, "Testing Therapeutic Hypotheses in Mice and Man: Observtions on the Therapeutic Activity Against Advanced Solid Tumors of Mice Treated with Anticancer Drugs that Have Demonstrated or Potential Clinical Utility for Treatment of Advanced Solid Tumors of Man," *Cancer Drug Development, Part B. Methods in Cancer Research*, vol. 17, pp. 3–51 (1979).

* cited by examiner

Primary Examiner—Jerome D. Goldberg
(74) Attorney, Agent, or Firm—Finnegan, Henderson, Farabow, Garrett, & Dunner LLP

(57) ABSTRACT

The present invention relates to a new pharmaceutical form of taxoid derivatives, and more particularly to the oral administration of a taxoid bearing two alkoxy groups in position 7 and 10.

8 Claims, No Drawings

USE OF TAXOID DERIVATIVES

This application claims the benefit of U.S. Provisional Application No. 60/121,333 filed Feb. 23, 1999.

The present invention relates to a new pharmaceutical form of taxoid derivatives. More precisely, it relates to the oral administration of a compound of general formula (I) or a pharmaceutically acceptable salt or solvent thereof:

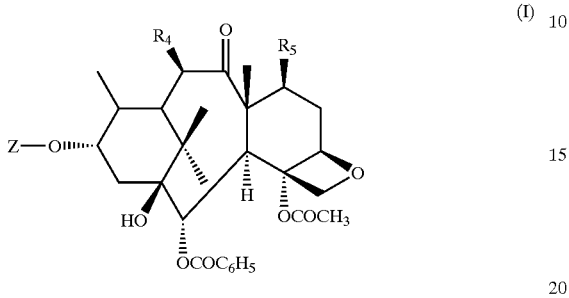

in which:

Z represents a hydrogen atom or a radical of general formula:

in which:

$R_1$ represents a benzoyl radical optionally substituted with one or more identical or different atoms or radicals chosen from halogen atoms, alkyl radicals comprising 1 to 4 carbon atoms, alkoxy radicals comprising 1 to 4 carbon atoms, and trifluoromethyl radicals, a thenoyl or furoyl radical, a radical $R_2$—O—CO— in which $R_2$ represents:

an alkyl radical comprising 1 to 8 carbon atoms, an alkenyl radical comprising 2 to 8 carbon atoms, an alkynyl radical comprising 3 to 8 carbon atoms, a cycloalkyl radical comprising 3 to 6 carbon atoms, a cycloalkenyl radical comprising 4 to 6 carbon atoms, or a bicycloalkyl radical comprising 7 to 61 carbon atoms, these radicals being optionally substituted with one or more identical or different substituents chosen from halogen atoms, hydroxyl radicals, alkoxy radicals comprising 1 to 4 carbon atoms, dialkylamino radicals in which each alkyl portion comprises 1 to 4 carbon atoms, piperidino or morpholino radicals, 1-piperazinyl radicals which are optionally substituted at position 4 with an alkyl radical comprising 1 to 4 carbon atoms or with a phenylalkyl radical in which the alkyl portion comprises 1 to 4 carbon atoms, cycloalkyl radicals comprising 3 to 6 carbon atoms, cycloalkenyl radicals comprising 4 to 6 carbon atoms, phenyl radicals which are optionally substituted with one or more identical or different atoms or radicals chosen from halogen atoms, alkyl radicals comprising 1 to 4 carbon atoms, and alkoxy radicals comprising 1 to 4 carbon atoms, cyano or carboxyl radicals, and alkoxycarbonyl radicals in which the alkyl portion comprises 1 to 4 carbon atoms, a phenyl or α- or β-naphthyl radical optionally substituted with one or more identical or different atoms or radicals chosen from halogen atoms, alkyl radicals comprising 1 to 4 carbon atoms and alkoxy radicals comprising 1 to 4 carbon atoms, a 5-membered aromatic heterocyclic radical, preferably chosen from furyl and thienyl radicals, or a saturated heterocyclic radical comprising 4 to 6 carbon atoms, and optionally substituted with one or more identical or different alkyl radicals comprising 1 to 4 carbon atoms;

$R_3$ represents an unbranched or branched alkyl radical comprising 1 to 8 carbon atoms, an unbranched or branched alkenyl radical comprising 2 to 8 carbon atoms, an unbranched or branched alkynyl radical comprising 2 to 8 carbon atoms, a cycloalkyl radical comprising 3 to 6 carbon atoms, a phenyl or α- or β-naphthyl radical optionally substituted with one or more identical or different atoms or radicals chosen from halogen atoms and alkyl, alkenyl, alkynyl, phenyl, α- or β-naphthyl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, it being understood that the alkyl radicals and alkyl portions of radicals comprise 1 to 4 carbon atoms, and the alkenyl and alkynyl radicals comprise 2 to 8 carbon atoms, or a 5-membered aromatic heterocyclic radical comprising one or more identical or different hetero atoms chosen from nitrogen, oxygen and sulphur atoms, and optionally substituted with one or more identical or different substituents chosen from halogen atoms and alkyl, phenyl, α- or β-naphthyl, alkoxy, aryloxy, amino, alkylamino, dialkylamino, acylamino, alkoxycarbonylamino, acyl, arylcarbonyl, cyano, carboxyl, carbamoyl, alkylcarbamoyl, dialkylcarbamoyl and alkoxycarbonyl radicals, it being understood that the alkyl radicals and alkyl portions of radicals comprise 1 to 4 carbon atoms, and the alkenyl and alkynyl radicals comprise 2 to 8 carbon atoms;

$R_4$ represents an alkoxy radical comprising 1 to 6 carbon atoms in an unbranched or branched chain, an alkenyloxy radical comprising 3 to 6 carbon atoms in an unbranched or branched chain, an alkynyloxy radical comprising 3 to 6 carbon atoms in an unbranched or branched chain, a cycloalkyloxy radical comprising 3 to 6 carbon atoms, or a cycloalkenyloxy radical comprising 4 to 6 carbon atoms, these radicals being optionally substituted with one or more identical or different halogen atoms or with an alkoxy radical comprising 1 to 4 carbon atoms, an alkylthio radical comprising 1 to 4 carbon atoms, a carboxyl radical, an alkyloxycarbonyl radical in which the alkyl portion comprises 1 to 4 carbon atoms, a cyano or carbamoyl radical, or an N-alkylcarbamoyl or N,N-dialkylcarbamoyl radical in which each alkyl portion comprises 1 to 4 carbon atoms or in which each alkyl portion forms, with the nitrogen atom to which it is attached, a saturated 5- or 6-membered heterocyclic radical optionally comprising a second hetero atom chosen from oxygen, sulphur and nitrogen atoms, and optionally substituted with an alkyl radical comprising 1 to 4 carbon atoms, a phenyl radical or a phenylalkyl radical in which the alkyl portion comprises 1 to 4 carbon atoms;

$R_5$ represents an alkoxy radical comprising 1 to 6 carbon atoms in an unbranched or branched chain, an alkenyloxy radical comprising 3 to 6 carbon atoms, an alkynyloxy radical comprising 3 to 6 carbon atoms, a cycloalkyloxy radical comprising 3 to 6 carbon atoms, or a cycloalkenyloxy radical comprising 3 to 6 carbon atoms, these radicals being optionally substituted with one or more identical or different halogen atoms or with an alkoxy radical comprising 1 to 4 carbon atoms, an alkylthio radical comprising 2 to 4 carbon atoms, a carboxyl radical, an alkyloxycarbonyl radical in which the alkyl portion comprises 1 to 4 carbon atoms, a cyano or carbamoyl radical, or an N-alkylcarbamoyl or N,N-dialkylcarbamoyl radical in which each alkyl portion comprises 1 to 4 carbon atoms or in which each alkyl portion forms, with the nitrogen atom to which it is attached, a saturated 5- or 6-membered heterocyclic radical optionally comprising a second hetero atom chosen from oxygen, sulphur and nitrogen atoms, and optionally substituted with an alkyl radical comprising 1 to 4 carbon atoms, a phenyl radical or a phenylalkyl radical in which the alkyl portion comprises 1 to 4 carbon atoms.

Preferably, $R_3$ is an aryl radical represented by a phenyl or α- or β-naphthyl radical optionally substituted with one or more identical or different atoms or radicals chosen from fluorine, chlorine, bromine, and iodine atoms, and alkyl, alkenyl, alkynyl, phenyl, α- or β-naphthyl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, it being understood that the alkyl radicals and alkyl portions of the other radicals comprise 1 to 4 carbon atoms, and the alkenyl and alkynyl radicals comprise 2 to 8 carbon atoms.

Preferably, $R_3$ can also be a 5-membered aromatic heterocyclic radical comprising one or more identical or different hetero atoms chosen from nitrogen, oxygen and sulphur atoms, and optionally substituted with one or more identical or different substituents chosen from fluorine, chlorine, bromine, and iodine atoms, alkyl radicals comprising 1 to 4 carbon atoms, aryl radicals comprising 6 to 10 carbon atoms, alkoxy radicals comprising 1 to 4 carbon atoms, aryloxy radicals comprising 6 to 10 carbon atoms, amino radicals, alkylamino radicals comprising 1 to 4 carbon atoms, dialkylamino radicals in which each alkyl portion comprises 1 to 4 carbon atoms, acylamino radicals in which the acyl portion comprises 1 to 4carbon atoms, alkoxycarbonylamino radicals comprising 1 to 4 carbon atoms, acyl radicals comprising 1 to 4 carbon atoms, arylcarbonyl radicals in which the aryl portion comprises 6 to 10 carbon atoms, cyano, carboxyl or carbamoyl radicals, alkylcarbamoyl radicals in which the alkyl portion comprises 1 to 4 carbon atoms, dialkylcarbamoyl radicals in which each alkyl portion comprises 1 to 4 carbon atoms or alkoxycarbonyl radicals in which the alkoxy portion comprises 1 to 4 carbon atoms.

Preferably, the radicals $R_4$ and $R_5$, which may be identical or different, represent unbranched or branched alkoxy radicals comprising 1 to 6 carbon atoms, and optionally substituted with a methoxy, ethoxy, ethylthio, carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl or N-piperidinocarbonyl radical.

More specifically, the present invention relates to the compounds of formula (I) in which Z represents a hydrogen atom or a radical of formula (II) in which $R_1$ represents a benzoyl radical or a radical $R_2$—O—CO— in which $R_2$ represents a tert-butyl radical; $R_3$ represents an alkyl radical comprising 1 to 6 carbon atoms,an alkenyl radical comprising 2 to 6 carbon atoms, a cycloalkyl radical comprising 3 to 6 carbon atoms, a phenyl radical optionally substituted with one or more identical or different atoms or radicals chosen from fluorine and chlorine atoms, and methyl, methoxy, dimethylamino, acetylamino, tert-butoxycarbonylamino, trifluoromethyl, 2- or 3-furyl, 2- or 3-thienyl and 2-, 4- or 5-thiazolyl radicals; and $R_4$ and $R_5$, which may be identical or different, represent an unbranched or branched alkoxy radical comprising 1 to 6 carbon atoms.

Still more specifically, the present invention relates to the compounds of formula (I) in which Z represents a hydrogen atom or a radical of formula (II) in which $R_1$ represents a benzoyl radical or a radical $R_2$—O—CO— in which $R_2$ represents a tert-butyl radical, $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and $R_4$ and $R_5$, which may be identical or different, represent a methoxy, ethoxy or propoxy radical.

Of even more special interest are the compounds of formula (I) in which Z represents a radical of formula (II) in which $R_1$ represents a tert-butoxycarbonyl radical, $R_3$ represents a phenyl radical, and $R_4$ and $R_5$, which may be identical or different, represent a methoxy, ethoxy or propoxy radical.

Still more particularly, the present invention relates to 4α-acetoxy-2α-benzoyloxy-5β,20-epoxy-1β-hydroxy-7β,10β-dimethoxy-9-oxo-11-taxen-13α-yl (2R,3S)-3 tert-butoxycarbonylamino-2-hydroxy-3-phenylpropionate of formula (Ia)

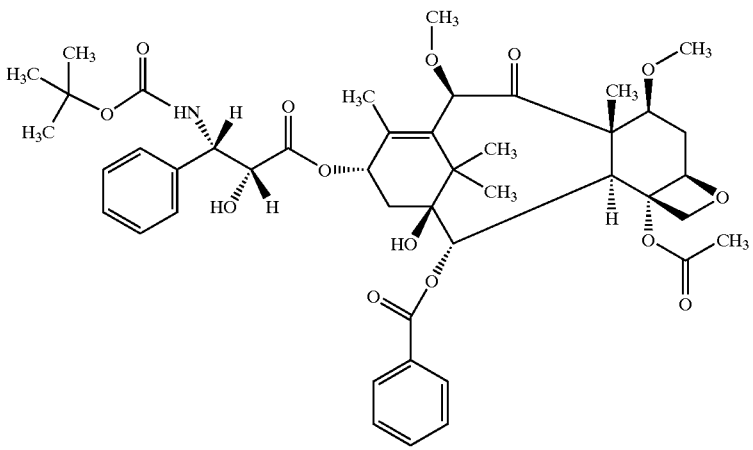

It is known, from International Publication WO96/30355, the disclosure of which is incorporated by reference herein, how to prepare a compound according to the present invention by two processes. According to a first, multi-step process, 10-deacetylbaccatin III of formula (III):

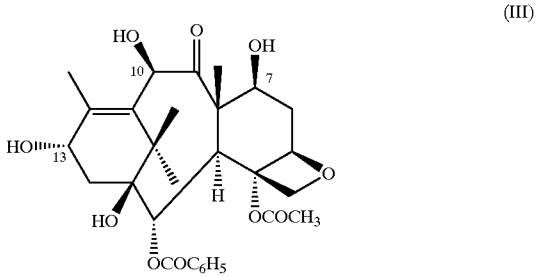

(III)

is selectively protected in positions 7 and 13, for example with a silyl diether, and then reacted with a compound of general formula (IV):

in which R represents a radical such that —OR has the same meaning as $R_4$ defined above, and X represents a reactive ester residue such as a sulphuric or sulphonic ester residue or a halogen atom, to give a compound bearing the unit —OR in position 10 and silyl groups in positions 7 and 13. Next, the silyl protecting groups are replaced with hydrogen atoms to give a compound still bearing the group —OR in position 10 and —OH groups in positions 7 and 13. The latter derivative is etherified selectively in position 7 by reaction with the compound of formula (IV) in which R represents a radical such that —OR has the same meaning as $R_5$ defined above, to give the compound of formula (I) in which Z is equal to hydrogen.

The next step comprises esterifying position 13, according to any known process in which the derivatives of formula (I), in which Z represents hydrogen, are reacted in the presence of a β-lactam, for example, according to the process described in European patent 617,018, the disclosure of which is incorporated by reference herein, or in the presence of an oxazolidine as described, for example, in International Publication WO 96/30355 mentioned above. After deprotection of the protecting groups in positions 7 and 10, an ester of formula (I) is obtained in which Z is other than hydrogen and R represents hydrogen. The next step comprises reacting the positions 7 and 10 simultaneously by the action of a reagent formed in situ from a sulphoxide of formula (V) and acetic anhydride (Pummerer-type reaction):

(V)

in which R represents a radical such that —OR has the same meaning as $R_4$ or $R_5$ defined above, to form an alkylthioalkyloxy-type intermediate on positions 7 and 10.

The final step, which allows the desired compound of formula (Ia) to be obtained, is carried out on the intermediate compound obtained above, by the action of activated Raney nickel.

Generally, the action of the reagent formed in situ from a sulphoxide of formula (V), preferably dimethyl sulphoxide and acetic anhydride, is carried out in the presence of acetic acid or an acetic acid derivative such as haloaetic acid, at a temperature ranging from 0 to 50° C.

Generally, the action of the activated Raney nickel in the presence of an aliphatic alcohol or an ether is carried out at a temperature of between −10 and 60° C.

In French patent application FR 97-14442, the disclosure of which is incorporated by reference herein, another process for preparing a derivative according to the present invention has been described. This process allows, in a single step, the direct, selective and simultaneous alkylation of the two hydroxyl functions in positions 7 and 10 of formula (VI) below:

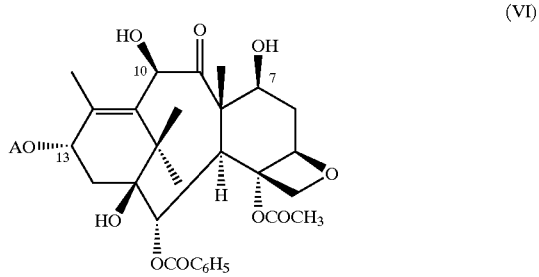

(VI)

in which A represents hydrogen or a side chain of formula (IIa) below:

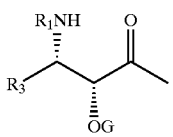

(IIa)

in which G represents a hydroxy protecting group, and $R_1$ and $R_3$ have the same meaning as in formula (II) above, or an oxazolidine unit of formula (IIb):

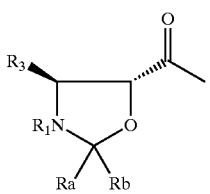

(IIb)

in which $R_1$ and $R_3$ have the same meaning as in formula (II), and $R_a$ and $R_b$, which may be identical or different, represent hydrogen or alkyl, aryl, halo, alkoxy, arylalkyl, alkoxyaryl, haloalkyl, or haloaryl substituents, it being possible for the substituents to optionally form a 4- to 7-membered ring.

It is preferred to use 10-deacetylbaccatin, i.e., the product of formula (III), as starting material, as the resulting process is more economical. It also avoids the intermediate protection and deprotection steps necessary in the known processes.

The hydroxy protecting groups G in formula (IIa) can be chosen from all of the hydroxy protecting groups described in books such as Greene and Wuts, Protective Groups in Organic Synthesis, 1991, John Wiley & Sons, and MacOmie, Protective Groups in Organic Chemistry, 1975, Plenum Press, the disclosures of which are incorporated by reference herein, so long as they can be deprotected under conditions which minimally degrade, or do not degrade, the rest of the molecule. For example, the following protecting groups may be used:

ethers, preferably ethers such as methoxymethyl ether, 1-ethoxyethyl ether, benzyloxymethyl ether, p-methoxybenzyloxymethyl ether, benzyl ethers optionally substituted with one or more identical or different groups such as methoxy, chloro, or nitro, 1-methyl-1-methoxyethyl ether, 2-(trimethylsilyl) ethoxymethyl ether, tetrahydropyranyl ether and silyl ethers such as trialkylsilyl ethers, and carbonates such as trichlorethyl carbonates.

More particularly, the radicals $R_a$ and $R_b$ of formula (IIb) are chosen from those described in International Publication WO 94/07878, the disclosure of which is incorporated by reference herein. The derivatives more particularly preferred are those in which $R_a$ is hydrogen and $R_b$ is a p-methoxyphenyl radical.

The alkylating agent is chosen from:
alkyl halides, preferably from alkyl iodides (RI),
alkyl sulphates, such as methyl sulphate, and
oxoniums, such as trialkyloxonium boric salts, in particular trimethyloxonium tetrafluoroborate ($Me_3OBF_4$).

Methyl iodide is preferably used as the alkylating agent.

The alkylating agent is used in the presence of an anionization agent such as one or more strong bases, in anhydrous medium.

Among the bases which can be used in anhydrous medium, mention may be made of:
alkali metal hydrides, such as sodium or potassium hydride,
alkali metal alkoxides, such as potassium tert-butoxide,
silver oxide $Ag_2O$,
1,8-bis(dimethylamino)naphthalene, and
mono- or dimetallic base mixtures, such as those described, for example, in publications such as P. Caubère Chem. Rev. 1993, 93, 2317–2334. or M. Schlosser Mod. Synth. Methods (1992), 6, 227–271, the disclosures of which are incorporated by reference herein. The alkyllithium/alkali metal t-butoxide or alkali metal amide/alkali metal t-butoxide combinations are particularly preferred. One of the two bases can be generated "in situ".

Among all of the possible combinations of alkylating agent and anionization agent, it is preferred to use methyl iodide in the presence of potassium hydride.

The reaction is preferably carried out in an organic medium which is inert under the reaction conditions. Among the solvents, it is preferred to use:
ethers such as tetrahydrofuran or dimethoxyethane;
when silver oxide is used as the anionization agent, it is preferred to use polar aprotic solvents such as dimethylformamide, or aromatic solvents such as toluene; and
when 1,8-bis(dimethylamino)naphthalene is used as the anionization agent, it is preferred to use alkylesters such as ethylacetate.

Preferably, the molar ratio between the anionization agent and the substrate is greater than 2, and more preferably ranges from 2 to 20.

It is also preferred that the molar ratio between the alkylating agent and the substrate is greater than 2, and preferably ranges from 2 to 40.

It is preferred to use a reaction temperature ranging from $-30°$ C. to $80°$ C.

The reaction time advantageously ranges from a few hours to 48 hours depending on the reagents chosen.

After the alkylating step is carried out on 10-deacetylbaccatin, the resulting compound can then be esterified according to known processes, for example, those described in European patent EP 617,018 or International Publication WO 96/30355, mentioned above.

Thus, according to a first, 3-step process, the procedure begins with the dialkylation of 10-deacetylbaccatin, using an alkylating agent in the presence of a strong base. In the second step, described in European patent 617,018 mentioned above, the 10-deacetylbaccatin dietherified in positions 7 and 10 is coupled, in position 13, with a suitably protected β-lactam in the presence of an activating agent chosen from tertiary amines and metal bases which ensure the formation of an alkoxide in position 13. Deprotection of the side chain is then achieved by the action of an inorganic or organic acid.

According to a second, 3-step process, the procedure can also begin with the dialkylation of 10-deacetylbaccatin, using an alkylating agent in the presence of a strong base. However, in the second step, described in International Publication WO 96/30355, the 10-deacetylbaccatin dietherified in positions 7 and 10 is coupled, in position 13, with an oxazolidine in the presence of a coupling agent such as diimides in the presence of an activating agent such as dialkylaminopyridines. Opening of the oxazolidine is achieved by the action of an inorganic or organic acid.

According to a third process, a baccatin suitably protected in positions 7 and 10 is esterified in position 13 with a β-lactam or an oxazolidine in the presence of a coupling agent and/or an activating agent as described in the above two processes. After deprotection in positions 7 and 10, the dietherification in positions 7 and 10 is carried out by an alkylating agent in the presence of a strong base. Deprotection of the side chain is then achieved by the action of an inorganic or organic acid.

Formulations suitable for oral administration mean formulations which are in a form suitable to be administered orally to a patient. The formulations may be presented as any suitable oral dosage form, such as, for example, capsules, cachets or tablets, each comprising a predetermined amount of the active ingredient, a powder or granules, a solution or a suspension in an aqueous liquid or a non-aqueous liquid, and an oil-in-water liquid emulsion or a water-in-oil liquid emulsion. The active ingredient may also be presented as a bolus, electuary or paste.

Pharmaceutical composition means a composition comprising a compound of formula (I) and at least one component chosen from pharmaceutically acceptable carriers, diluents, adjuvants, excipients, or vehicles, such as preserving agents, fillers, disintegrating agents, wetting agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, and mixtures of these substances. Prevention of the action of microorganisms can be ensured by various antibacterial and antifungal agents, for example, parabens, chlorobutanol, phenol, sorbic acid, and the like. Examples of suitable carriers, diluents, solvents or vehicles include water, ethanol, polyols, vegetable oils (such as olive oil), organic esters such as ethyl oleate, and suitable mixtures thereof. Examples of excipients include lactose, milk, sugar, sodium citrate, calcium carbonate, and dicalcium phosphate. Examples of disintegrating agents include starch, alginic acids and certain complex silicates. Examples of lubricants include magnesium stearate, sodium lauryl sulphate, talc, and high molecular weight polyethylene glycols.

Liquid dosage form means that the dose of the active compound to be administered to the patient is in liquid form, such as, for example, pharmaceutically acceptable emulsions, solutions, suspensions, syrups and elixirs. In addition to the active compounds, the liquid dosage forms may comprise inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols, fatty acid esters of sorbitan and phospholipids, a mixture of these substances, and the like.

Solid dosage form means the dosage form of the compound according to the invention is in solid form, such as, for example, capsules, tablets, pills, powders, dragees or granules. In such solid dosage forms, the compound according to the invention is admixed with at least one inert customary excipient (or carrier) such as sodium citrate or dicalcium phosphate or with (a) fillers or extenders, for example, starches, lactose, sucrose, glucose, mannitol and silicic acid, (b) binders, for example, carboxymethylcellulose, alignates, gelatin, polyvinylpyrrolidone, sucrose and acacia, (c) humectants, for example, glycerol, (d) disintegrating agents, for example, agar-agar, calcium carbonate, potato or tapioca starch, alginic acid, certain complex silicates and sodium carbonate, (e) solution retarders, for example paraffin, (f) absorption accelerators, for example, quaternary ammonium compounds, (g) wetting agents, for example, acetyl alcohol and glycerol monostearate, (h) adsorbents, for example, kaolin and bentonite, (i) lubricants, for example, talc, calcium stearate, magnesium stearate, solid polyethylene glycols and sodium lauryl sulfate, (j)pacifying agents, (k) buffering agents, or agents which release the compound according to the invention in a certain part of the intestinal tract in a delayed manner.

The invention will be more accurately defined by the following examples which must not be considered as limiting the present invention.

EXAMPLES

Formulation II: 0.2 mg/ml of the compound of formula (Ia) was mixed in a solution comprising 5% ethanol, 5% Polysorbate 80, and 90% of an aqueous 5% glucose solution.

15 female C3H/HeN mice, each weighing approximately 20 g, were each administered Formulation II orally in a dose of 20.6 mg.kg$^{-1}$ per administration per mouse, 12.8, 8.4 and 5.5 each day for 5 days.

Animals: The animals subjected to the experiment, generally mice, were subcutaneously grafted bilaterally with 30 to 60 mg of a mammary tumor fragment (adenocarcinoma MA17/A) on day 0. The animals bearing tumors were mixed before being assigned to the various treatment and control groups. Chemotherapy generally began from 3 to 7 days after grafting, depending on the type of tumour, and the animals were observed every day. The different animal groups were weighed 3 or 4 times a week until the maximum weight loss was attained, and the groups were then weighed at least once a week until the end of the trial.

Efficacy: The efficacy of the new pharmaceutical form was evaluated by:

the tumor growth inhibitor (T/C)

The T/C value in percent is an indication of antitumor effectiveness:

$$T/C(\%) = \frac{\text{Median tumor weight of the Treated}}{\text{Median tumor weight of the Control}} \times 100$$

According to NCI standards, a T/C<42% is the minimal level to declare activity. A T/C<10% is considered to indicate high antitumor activity and is the level used by NCI to justify further development (Decision Network-2 level, DN-2).

The T/C value can be converted to an arbitrary activity rating according to the NCI criteria:

| NCl activity | | % T/C |
|---|---|---|
| Highly active | ++ | <10 |
| Active | + | 11–42 |
| Inactive | – | >42 | and quantified by the log cell kill which is determined by the following formula:

$\log_{10}$ cells killed=$T-C$(days)/3.32×$T_d$ in which T–C represents the time in days for the tumors of the treated group (T) and the tumors of the non-treated group (C) to reach a predetermined value (750 mg for example). This method is described in T. H. CORBETT et al., Cancer, 40, 2660–2680 (1977); F. M. SCHABEL et al., Cancer Drug Development, Part B. Methods in Cancer Research, 17, 3–51New York Academic Press Inc. (1979), the disclosure of which is incorporated by reference herein. A product is considered to be active if $log_{10}$ cells killed is greater than or equal to 0.7. A product is considered to be very active if $log_{10}$ cells killed is greater than 2.8.

Results:

| Agent | Route volume | Dosage in mg/kg/dose | Schedule in days | Total dose in mg/kg | Drug death (days of death) | Average body weight change in % per mouse post last treatment (day) | Median tumor weight in mg on day 12 (range) | T/C in % day 12 | Time for median tumor to reach 750 mg in days | T-C in days | log cell kill | Comments |
|---|---|---|---|---|---|---|---|---|---|---|---|---|
| Product of formula IA | p.o. 0.2 ml | 20.6 | 3 to 7 | 103.0 | 5/5 (7,2d8,10,11) | — | — | — | — | — | — | Toxic |
| | | 12.8 | | 64.0 | 0/5 | −17.9 (10) | 0 (0–0) | 0 | 25.9 | 13.8 | 3.2 | HNTD highly active |
| | | 8.4 | | 42.0 | 0/5 | −11.0 (9) | 0 (0–268) | 0 | 18.2 | 6.1 | 1.4 | Active |
| | | 5.5 | | 27.5 | 0/5 | +0.2 (8 | 271 (107–432) | 38 | 14.4 | 2.3 | 0.5 | Inactive |
| Control | | | | | | | 704 (312–864) | | 12.1 | | | |

Tumor doubling time = 1.3 days 10 mice in the control group. Mice average weight (product of fomula Ia) = 20.39 g
Abbreviation used: HNTD = highest nontoxic dose
Comments: Product of IA was evaluated against early stage mammary adenocarcinoma MA17/A using a daily schedule for 5 days. At the highest toxic dose 12.8 mg/kg/administration (total dose 64 mg/kg), product Ia was found highly active in this tumor model with a 0% T/C and a 3.2 log cell kill total.

What is claimed is:

1. A method for treating abnormal cell proliferation sensitive to compounds of formula (I), said method comprising administering by an oral route to a mammal at least one compound of formula (I) or a pharmaceutically acceptable salt or solvent thereof in an amount effective for treating abnormal cell proliferation:

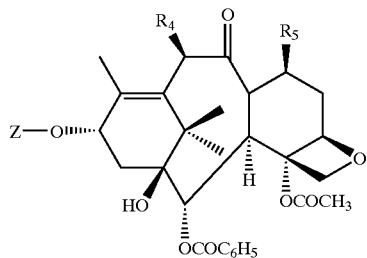

(I)

wherein:
Z is a hydrogen atom or a radical of formular

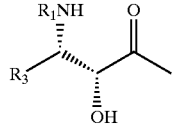

(II)

wherein:
$R_1$ is selected from:
a benzoyl radical optionally substituted with one or more identical or different atoms or radicals selected from halogen atoms and alkyl radicals comprising 1 to 4 carbon atoms, alkoxy radicals comprising 1 to 4 carbon atoms and trifluoromethyl radicals, and
a radical $R_2$—O—CO— wherein $R_2$ is a tert-butyl radical;
$R_3$ is:
a phenyl radical optionally substituted with one or more identical or different atoms or radicals selected from halogen atoms and alkyl, alkenyl, alkynyl, phenyl, α- or β-naphthyl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, wherein said alkyl radicals and alkyl portions of radicals comprise 1 to 4 carbon atoms, and wherein said alkenyl and alkynyl radicals comprise 2 to 8 carbon atoms;
$R_4$ is selected from methoxy, ethoxy, and propoxy radicals;
wherein said $R_4$ radicals are optionally substituted with one or more identical or different halogen atoms or with an alkoxy radical comprising 1 to 4 carbon atoms, an alkylthio radical comprising 1 to 4 carbon atoms, a carboxyl radical, an alkyloxycarbonyl radical wherein the alkyl portion comprises 1 to 4 carbon atoms, a cyano or carbamoyl radical, or an N-alkylcarbamoyl or N,N-dialkylcarbamoyl radical wherein each alkyl portion comprises 1 to 4 carbon atoms, or wherein said alkyl portion forms, with the nitrogen atom to which it is attached, a saturated 5- or 6-membered heterocyclic radical optionally comprising a second heteroatom selected from oxygen, sulfur and nitrogen atoms, and being optionally substituted with an alkyl radical comprising 1 to 4 carbon atoms, or a phenyl radical or a phenylalkyl radical wherein the alkyl portion comprises 1 to 4 carbon atoms; and
$R_5$ is selected from methoxy, ethoxy, and propoxy radicals;
wherein said $R_5$ radicals are optionally substituted with one or more identical or different halogen atoms, an alkoxy radical comprising 1 to 4 carbon atoms, an alkylthio radical comprising 2 to 4 carbon atoms, a carboxyl radical, an alkyloxycarbonyl radical wherein the alkyl portion comprises 1 to 4 carbon atoms, a cyano or carbamoyl radical, or an N-alkylcarbamoyl or N,N-dialkylcarbamoyl radical wherein each alkyl portion comprises 1 to 4 carbon atoms, or wherein said alkyl portion forms, with the nitrogen atom to which it is attached, a saturated 5- or 6-membered heterocyclic radical optionally comprising a second heteroatom selected from oxygen, sulfur and nitrogen atoms, and being optionally substituted with an alkyl radical comprising 1 to 4 carbon atoms, a phenyl radical or a phenylalkyl radical wherein the alkyl portion comprises 1 to 4 carbon atoms.

2. A method according to claim 1, wherein Z is a radical of formula (II) wherein $R_1$ is a tert-butoxycarbonyl radical, $R_3$ is a phenyl radical, and $R_4$ and $R_5$, which may be identical or different, are selected from methoxy, ethoxy and propoxy radicals.

3. The method of claim 1, wherein

Z is a hydrogen atom or a radical of formula (II)
  $R_1$ is a benzoyl radical or a radical $R_2$—O—CO—
  $R_2$ is a tertbutyl radical,
  $R_3$ is a phenyl radical optionally substituted with one or more identical or different atoms or radicals chosen from halogen atoms and alkyl, alkoxy, dialkylamino, acylamino, alkoxycarbonylamino, trifluoromethyl, and
  $R_4$ and $R_5$, which may be identical or different, are chosen from methoxy, ethoxy and propoxy radicals.

4. The method of claim 1, wherein at least one compound of formula (I) is 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenyl-propionate.

5. The method of claim 1, wherein the compound of formula (I), pharmaceutically acceptable salt, or solvent thereof is provided in a composition comprising one or more pharmaceutically acceptable carriers, diluents, adjuvants, excipients, or vehicles.

6. The method of claim 1, wherein the compound of formula (I), pharmaceutically acceptable salt, or solvent thereof is provided in a composition comprising one or more pharmaceutically acceptable preserving agents, fillers, binders, absorption accelerators, solution retarders, adsorbents, pacifying agents, buffering agents, delayed-release agents, disintegrating agents, wetting agents, perfuming agents, antibacterial agents, antifungal agents, lubricating agents, dispensing agents, suspending agents, solubilizing agents, or emulsifiers.

7. The method of claim 1, wherein the compound of formula (I), pharmaceutically acceptable salt, or solvent thereof is administered in a solid form.

8. The method of claim 1, wherein the compound of formula (I), pharmaceutically acceptable salt, or solvent thereof is administered in a liquid form.

* * * * *